United States Patent [19]

Japuntich

[11] Patent Number: 5,695,489
[45] Date of Patent: Dec. 9, 1997

[54] BLOOD FILTERING CONTAINER

[75] Inventor: John C. Japuntich, Lake Villa, Ill.

[73] Assignee: Baxter International Inc., Deerfield, Ill.

[21] Appl. No.: 768,493

[22] Filed: Sep. 30, 1991

[51] Int. Cl.$^6$ ............................................. A61M 1/00
[52] U.S. Cl. ........................... 604/406; 604/408; 604/403
[58] Field of Search .................................. 604/408, 405, 604/406, 122, 126, 403, 407, 410; 422/44, 45, 46, 47, 48; 215/DIG. 3

[56] References Cited

U.S. PATENT DOCUMENTS

| | | |
|---|---|---|
| 2,848,995 | 8/1958 | Ryan . |
| 3,492,991 | 2/1970 | Dyer, Jr. . |
| 3,507,395 | 4/1970 | Bentley . |
| 3,891,416 | 6/1975 | Leonard et al. ........................ 604/317 |
| 4,014,329 | 3/1977 | Welch et al. . |
| 4,021,353 | 5/1977 | Raines et al. . |
| 4,033,345 | 7/1977 | Sorenson et al. ........................ 604/406 |
| 4,033,724 | 7/1977 | Tamiya . |
| 4,047,526 | 9/1977 | Reynolds et al. . |
| 4,188,360 | 2/1980 | Kurata . |
| 4,228,125 | 10/1980 | Lobdell et al. . |
| 4,235,233 | 11/1980 | Mouwen . |
| 4,261,951 | 4/1981 | Milev ........................................ 422/46 |
| 4,437,472 | 3/1984 | Naftulin . |
| 4,443,220 | 4/1984 | Hauer et al. . |
| 4,572,724 | 2/1986 | Rosenberg et al. ........................ 55/159 |
| 4,573,992 | 3/1986 | Marx . |
| 4,710,165 | 12/1987 | McNeil et al. . |
| 4,734,269 | 3/1988 | Clarke et al. . |
| 4,798,578 | 1/1989 | Ranford . |
| 4,850,964 | 7/1989 | Cotter . |
| 4,863,452 | 9/1989 | Irmiter et al. ........................... 604/408 |
| 4,955,877 | 9/1990 | Kurtz et al. . |
| 4,976,707 | 12/1990 | Bodicky et al. ........................ 604/408 |
| 5,049,146 | 9/1991 | Bringham et al. ........................ 604/9 |
| 5,061,236 | 10/1991 | Sutherland et al. ........................ 604/4 |
| 5,087,250 | 2/1992 | Lichte et al. ........................... 604/321 |

FOREIGN PATENT DOCUMENTS 2101892   1/1983   United Kingdom .

*Primary Examiner*—Sam Rimell

[57] ABSTRACT

A device (10) for receiving, storing, filtering and reinfusing a patient's blood is described. The device is a flexible container that has two unique features in the preferred embodiment. One feature is the use of a filter (24) which filters blood immediately prior to reinfusing blood into a patient. The other feature is the use of a separating means (32) to prevent the filter from collapsing upon itself.

2 Claims, 4 Drawing Sheets

16# BLOOD FILTERING CONTAINER

BACKGROUND OF THE INVENTION

1. Field of the Invention

This invention relates generally to blood filter bags and more specifically relates to blood filter bags for receiving, storing, filtering and reinfusing a patient's blood.

2. Description of the Prior Art

In the medical field, it is frequently desirable to collect a patient's blood during and after surgery, store and filter the blood, and reinfuse the patient's filtered blood back to the patient rather than to administer blood from a blood bank. In most current applications of auto-transfusion, blood is collected directly from the wound, filtered and stored prior to reinfusion. The collected blood is frequently loaded with debris and clots that must be filtered out prior to reinfusion. Most current filtering techniques inadequately perform the necessary filtering because they have a tendency to become clogged during the filtering procedure. There are several reasons why a filter may become clogged. One reason is that the filter may have a relatively small surface area for performing the filtering procedure. Another reason is that the filter may collapse upon itself during the filtering process. Whenever a filter is collapsed upon itself, it will not be possible for blood to adequately flow through the filter. Therefore, a need existed to develop a device having a relatively large surface area for filtering and having a means for maintaining the surface area in an expanded, non-collapsed state to allow blood to flow freely therethrough.

Another problem associated with the currently used filtering devices is that they are generally designed to filter blood as it enters, rather than leaves, a storage container. Unfortunatelly, the stored blood may develop additional clots after it has been filtered, but prior to reinfusion. Currently used blood filter bags do not have a mechanism for filtering blood immediately prior to the time the blood leaves the bag. Therefore, a need existed to develop a device which provided a mechanism for filtering blood immediately prior to reinfusion.

Another problem frequently associated with currently used filtering devices is that many such devices have both the inlet and outlet ports located at the same end of the collection container. Although it is easier and less expensive to manufacture devices with both the inlet and outlet ports at the same end, such devices are more difficult to use because they must be rotated 180 degrees prior to reinfusing blood back into a patient. Therefore, one objective of the subject invention was to develop a device which did not require rotating the collection container between collecting and reinfusing a patient's blood.

SUMMARY OF THE INVENTION

A device is described for receiving, storing, filtering and reinfusing a patient's blood. The device includes a container having an inlet port to receive blood from a patient. The container also has an outlet port for reinfusing blood back into the patient. The container still further has a chamber between the inlet and outlet ports. The chamber forms a blood-flow path between the inlet and outlet ports. The blood flow path has a first collection and storage area adjacent to the inlet port. The blood flow path also has a second filtering area adjacent to the outlet port.

The device also includes a filter means for filtering blood. In a preferred embodiment, the filtering means is located in the filtering area and surrounds the outlet port to cause blood to be filtered immediately before blood leaves said chamber through said outlet port.

In another embodiment of the invention, the filtering means is not required to be located adjacent the outlet port. However, the filtering means includes a filtering material and a separating means for preventing the filtering material from collapsing upon itself. The separating means allows blood to flow through the filtering material as blood flows between the filtering area and the collection and storage area.

DETAILED DESCRIPTION OF THE PREFERRED EMBODIMENT

Figure 1:
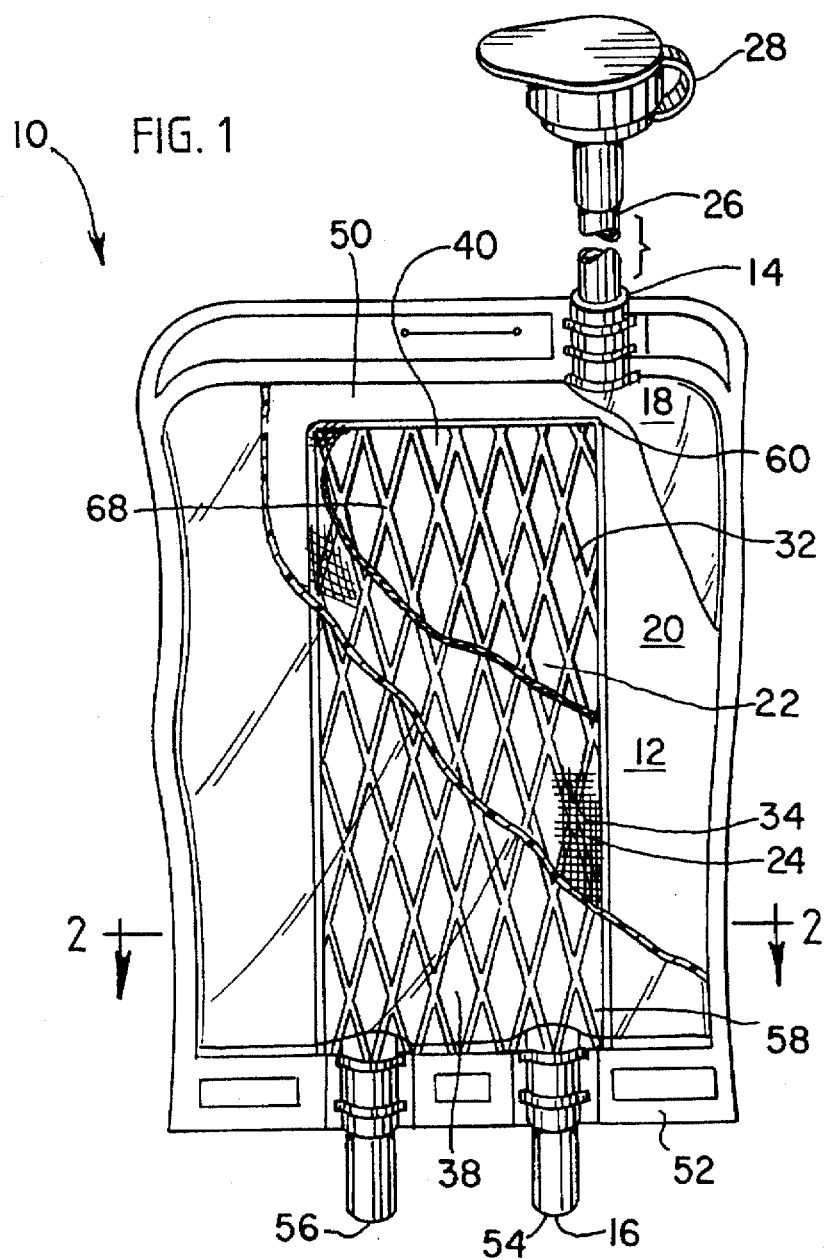
FIG. 1 is a perspective cut-away view of the preferred embodiment of the invention.

Refer now to FIG. 1 which is a perspective view of the subject invention. As can be seen in the figure, the invention is a device 10 for receiving, storing, filtering and reinfusing a patient's blood. The device includes a container 12 having an inlet port 14 to receive blood from a patient. The container 12 also includes an outlet port 16 for reinfusing blood back into the patient. The container 12 includes a chamber 18 between the inlet and outlet ports 14, 16. The chamber forms a blood flow path between the inlet and outlet ports. The blood flow path includes a first collection and storage area 20 adjacent the inlet port 14. The blood flow path also includes a second filtering area 22 adjacent the outlet port. The device 10 also includes a filter means 24 for filtering blood. The filter means 24 is located in the filtering area 22 and surrounds the outlet port 16 to cause blood to be filtered immediately before blood leaves the chamber 18.

In the preferred embodiment, the inlet port 14 is connected to a transfer tube 26. The distal end 28 of the transfer tube 26 is connected to a collection cannister (not shown). In normal operation, a patient's blood is first drained or suctioned into the collection cannister and then transferred into the device 10 through the transfer tube 26. Thus, a patient's blood enters the container 12 through the inlet port 14 and first flows into the collection and storage area 20. When it is desired to reinfuse the collected blood in container 12 back into a patient, an administration set having a final microaggregate filter is attached to the outlet port 16. The outlet port is a normally closed port which is opened when the administration set is attached to the port. This allows blood in the collection area 20 to flow into the second filtering area 22 and then into the outlet port 16. As the blood flows through the second filtering area 22, macro blood clots and debris are filtered and remain in the first collection and storage area 20.

Figure 2:
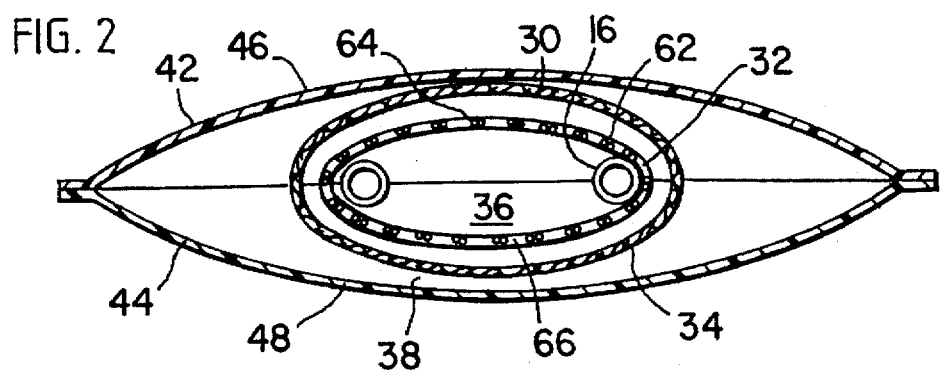
FIG. 2 is a cross-sectional view of the preferred embodiment of the invention taken along the line A—A of FIG. 1.

In the preferred embodiment, the filter means includes a filtering material 30 surrounding the outlet 16 (FIG. 2). The filtering means 24 also includes a separating means 32 for preventing the filtering material 30 from collapsing upon itself. If the filtering material collapses upon itself, blood will not be able to flow through the material to the outlet port 16. As can be seen in FIGS. 1 and 2, in the preferred embodiment of the invention, the filtering material is formed from a continuous filtering sheet 34 which completely surrounds the outlet port 16 to form a filtering region 36. The filtering region extends into the chamber 18 above the outlet port 16 toward the inlet port 14. The reason for having the filtering sheet 34 extend into the chamber 18 toward the inlet port is to provide a filtering surface area which extends upwardly from the outlet port 16. This is advantageous because macro blood clots and debris tend to collect in the bottom of the container 12 and would clog a filter which covered only the lower portion of the container. Therefore, since the filtering sheet extends vertically upward into the chamber 18 as blood clots and debris collect in the bottom of the chamber and clog the lower portions of the filtering sheet, the upper portion of the filtering sheet will remain available for allowing blood to pass therethrough.

In the preferred embodiment of the invention, the filtering region 36 extends at least five centimeters upwardly from the outlet port 16 to allow clots and debris to collect around a lower portion 38 of the filtering region 36 adjacent the outlet port 16 and to continue to allow blood to flow through an upper portion 40 of the filtering region extending above the collected debris and clots.

In the preferred embodiment, the filtering material 30 is formed of a hydrophobic substance. The reason for having the filtering material formed from a hydrophobic substance is to prevent the filtering material from absorbing fluid from the patient's blood which would cause the filter to clog. In one embodiment, the filtering material has a pore size ranging from 150 to 250 microns. Preferably, the pore size will range from 210 to 230 microns. In the preferred embodiment, the filtering material 30 is formed using a medical-grade sterilizable nylon.

The container 12 in the preferred embodiment is formed using two sheets 42, 44 of pliable material such as polyvinylchloride (PVC). The sheets 42, 44 are sealed about the periphery to form a relatively flat container 12 having a front wall 46 and a back wall 48. The container 12 also has a top 50 and a bottom 52 as seen in FIG. 1. In the preferred embodiment, the inlet port 14 is located along the top 50 of the container 12 and the outlet port 16 is located along the bottom 52 of the container 12. Preferably, both the inlet and outlet ports are sealed between the front and back walls 46, 48. In the preferred embodiment, multiple outlet ports 54, 56 may be provided along the bottom 52 of the container 12 between the seal. Multiple outlet ports 54, 56 are provided as an industry standard to allow for the rapid reinfusion of a patient's blood.

As can be seen in FIGS. 1 and 2, the filtering material 30 which surrounds the outlet port 16 is in the shape of a tube. A bottom end 58 of the tube adjacent the outlet port 16 is sealed around the outlet port. If multiple outlet ports are used, the bottom end 58 of the filtering material tube will be sealed around each of the outlet ports 54, 56. In the preferred embodiment, the top end 60 of the tube is also closed. Thus, in order for blood to enter into the filtering region 36, blood must pass through the continuous filtering sheet 34.

One advantage of the subject invention over other blood filter bags is that a separating means 32 is provided which keeps the filtering material from collapsing upon itself as blood flows through the filtering material. In the preferred embodiment, the separating means is formed from a tube-shaped mesh 62. The mesh is located between the filtering sheet 34 and the outlet port 16 and extends substantially throughout the filtering region 36. The mesh can be formed of any material which is hydrophobic and flexible yet is resistant to totally collapsing upon itself. It is desirable that the mesh be hydrophobic in order for it to be resistant to absorbing blood. It is important for the mesh to be resistant to totally collapsing upon itself so that it will separate and support the filtering sheet 34 as blood flows through the sheet and mesh 62 to the outlet port 16.

In the preferred embodiment, the mesh is formed of a medical-grade, sterilizable polypropylene webbed tube. The tube is partially collapsible upon itself to form a pair of parallel walls 64, 66 that are separated from one another within the filtering region 36. In the preferred embodiment, the walls extend substantially throughout the filtering region 36 to prevent the filtering sheet 34 from collapsing upon itself.

In the preferred embodiment, the mesh 62 is formed of interconnecting diamonds 68. Each diamond is formed of a polypropylene filament having a diameter ranging from 0.025" to 0.035". When the mesh is in a relaxed position, each diamond has a width ranging from 0.15" to 0.25" and a height ranging from 0.4" to 0.8". The mesh is expandable in width but not expandable or compressible in height. It is important that the mesh be not expandable or compressible in height because this feature causes the mesh to maintain its vertical position within the filtering region as blood clots and other debris collect which would otherwise cause a compressible mesh to collapse.

Figure 3:
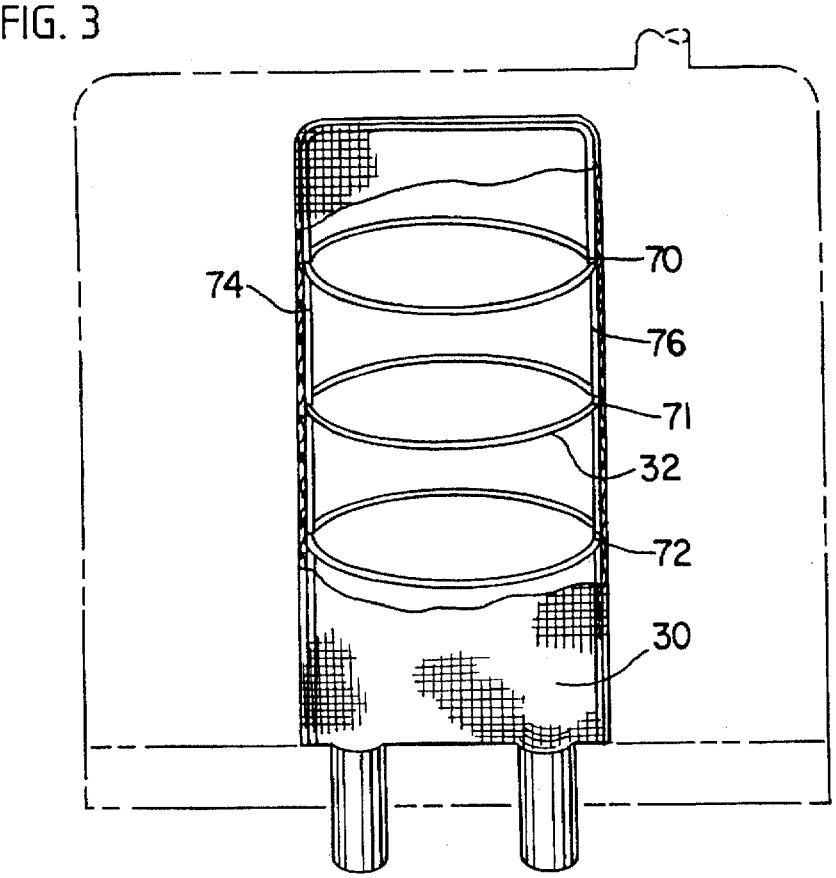
FIG. 3 is a perspective cut-away view of another alternative embodiment of the subject invention in which the separating means is a plurality of spaced-apart rings.

Refer now to FIG. 3, which is an alternative embodiment of the invention. In this figure, the separating means 32 is formed using multiple rings 70–72 that are spaced apart from each other and located in the filtering region 36 to prevent the filtering material 30 from collapsing upon itself. The rings 70–72 can be spaced apart from each other by spacer bars 74, 76 or by attaching each of the rings to the filtering material 30 at predetermined, spaced apart locations.

Figure 4:
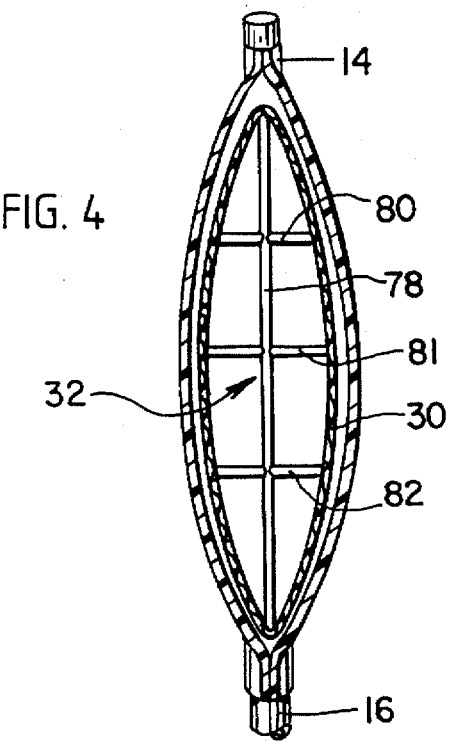
FIG. 4 is a perspective view of one embodiment in which the separating means is formed using a central vertically extending bar and a plurality of horizontally extending bars connected thereto.

In another embodiment of the invention, as illustrated in FIG. 4, the separating means 32 is formed using a central vertically extending bar 78 with multiple horizontal bars 80, 82 extending outwardly therefrom. The bars are located in the filtering region 36 to prevent the filtering material 30 from collapsing upon itself.

Figure 5:
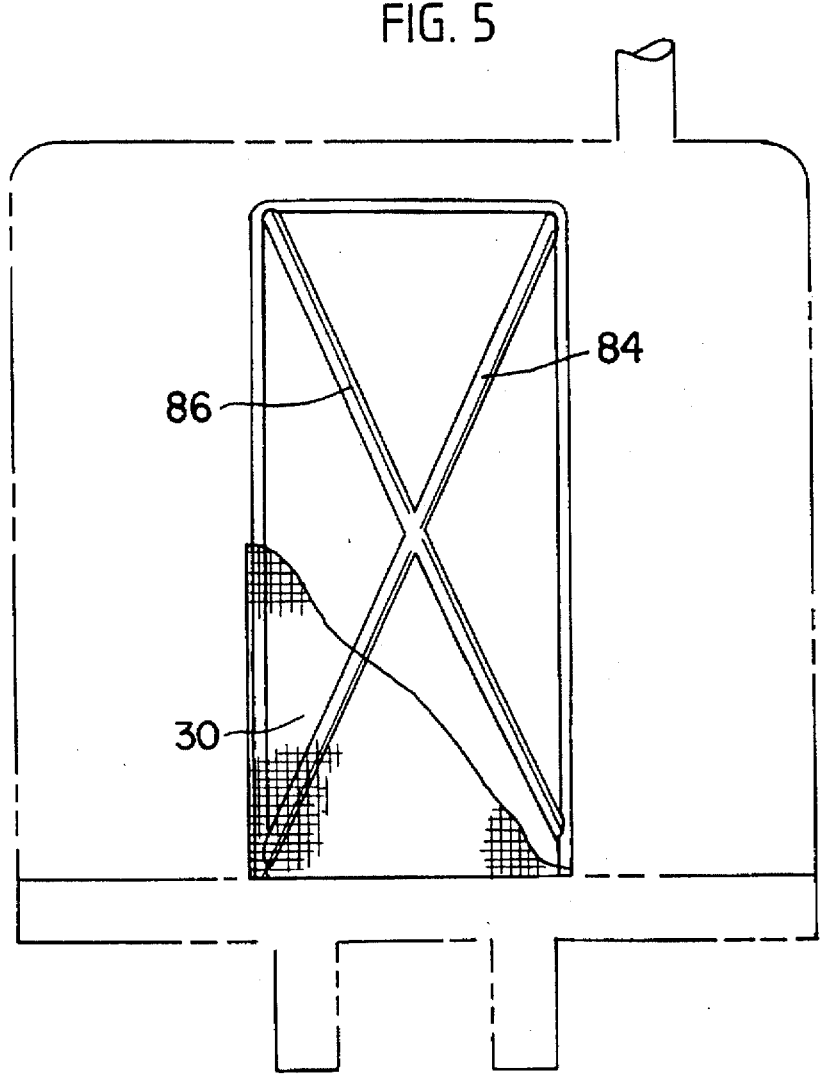
FIG. 5 is a perspective view of one embodiment of the invention in which the separating means is formed using a pair of diagonally extending crossed bars.

In yet another embodiment of the invention, as illustrated in FIG. 5, the separating means is formed using a pair of diagonally extending crossed bars 84, 86. These bars extend outwardly from the center of the filtering region to the opposite ends of the filtering region to prevent the filtering material 30 from collapsing upon itself.

Figure 6:
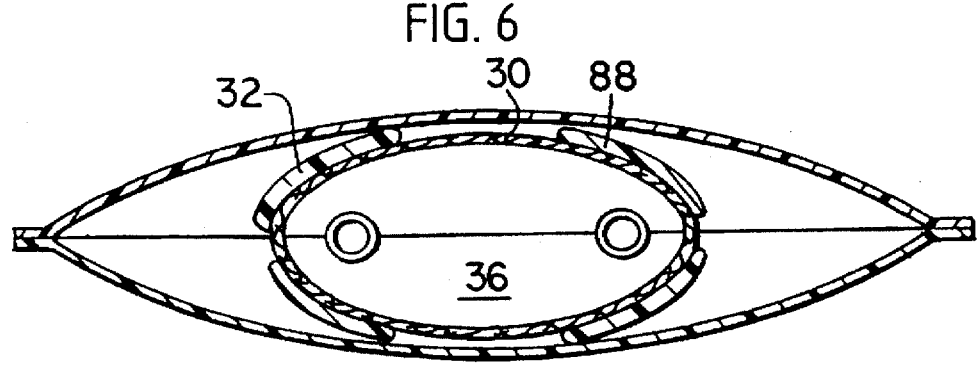
FIG. 6 is a cross-sectional view of yet another embodiment of the invention in which the separating means is formed using a frame.

In yet another embodiment of the invention, illustrated in FIG. 6, the separating means 32 may be formed using an external supporting frame 88. The filtering material 30 is attached to the frame 88 in the filtering region 36 to prevent the filtering material 30 from collapsing upon itself.

Figure 7:
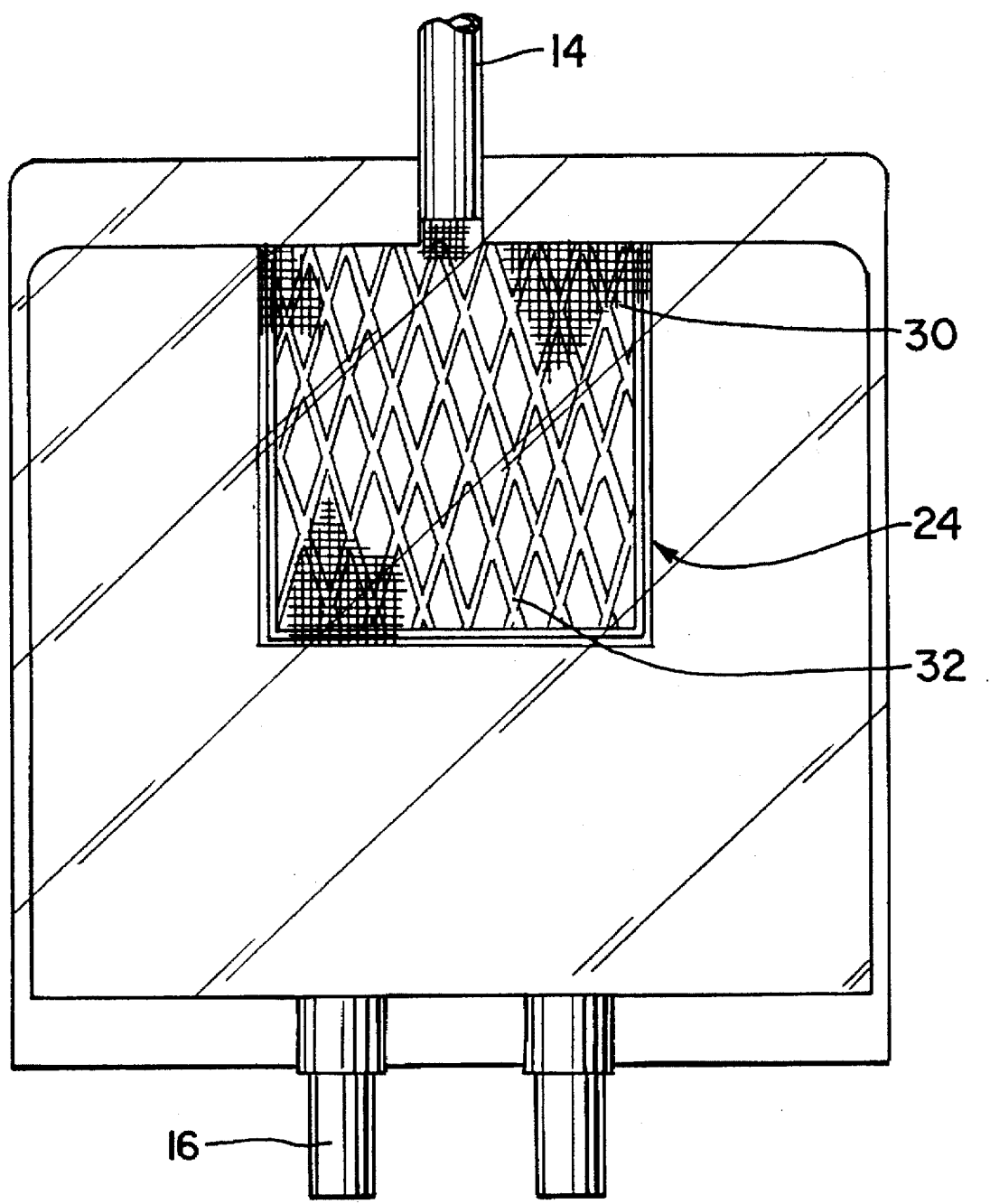
FIG. 7 is a perspective view of an alternative embodiment of the subject invention in which the filtering means is located adjacent the inlet port.

Refer now to FIG. 7 which is an alternative embodiment of the subject invention. In this embodiment of the invention the filter means is located adjacent the inlet port 14 rather than the outlet port 16. The filter means 24 is unique in this embodiment in that it includes a separating means 32 similar to any of the separating means described above.

While the invention has been described in detail and with reference to specific embodiments thereof, it will be apparent to those skilled in the art that various changes and modifications can be made therein without departing from the spirit and scope of the invention.

I claim:

1. A device (10) for receiving, storing, filtering and reinfusing a patient's blood, comprising:
   (A) a container (12) having
      (i) an inlet port (14) to receive blood from a patient,
      (ii) an outlet port (16) for re-infusing blood back into a patient,
      (iii) a chamber (18) between said inlet and outlet ports forming a blood flow path between said inlet and outlet ports, said blood flow path having
         (a) a first collection and storage area (20) adjacent said inlet port; and
         (b) a second filtering area (22) adjacent said outlet port; and
   (B) filter means (24) for filtering blood, said filter means sealed around said outlet port to form said filtering area, and to cause said blood to be filtered immediately before said blood leaves said chamber (18) said filter means further including:
   a filtering material (30) surrounding said outlet port; said filtering material made from a continuous filtering sheet (34) completely surrounding said outlet port to form an enclosed filtering region (36) extending into said chamber (18) above said outlet port (16) toward said inlet port (14) wherein said filtering region (36) extends at least five centimeters upwardly from said outlet port to allow clots and debris to collect around a lower portion (38) of said filtering region (36) adjacent said outlet port (16) and to continue to allow blood to flow through an upper portion (40) of said filtering region extending above said collected debris and clots; and separating means (32) for preventing said filtering material from collapsing upon itself thereby allowing blood to flow from said collection and storage area through said filtering material to said outlet port wherein said separating means (32) further comprises:

a tubular mesh (62), said mesh being located between said filtering sheet (34) and said outlet port and extending substantially throughout said filtering region (36), and said mesh being flexible, yet resistant to totally collapsing upon itself and resistant to absorbing blood, said mesh (62) being formed of a medical-grade, sterilizable, polypropylene webbed tube that is partially collapsible upon itself to form a pair of parallel walls that are separated from one another within said filtering region, said walls extending substantially throughout said filtering region to prevent said filtering sheet from collapsing upon itself, thereby separating and supporting said filtering sheet (34) to allow blood to flow freely through said mesh (62).

2. A device for receiving, storing, filtering and reinfusing a patient's blood as recited in claim 1, wherein:

said mesh (62) is formed of interconnecting diamonds (68), each diamond being formed of a polypropylene filament having a diameter ranging from 0.025" to 0.035" and each diamond having a width ranging from 0.15" to 0.25" and a height ranging from 0.4" to 0.8" when said is in a relaxed position, said mesh being expandable in width and being non-expendable or compressible in height.

* * * * *